United States Patent
Kuenzl et al.

(10) Patent No.: US 9,903,847 B2
(45) Date of Patent: Feb. 27, 2018

(54) SENSOR DEVICE FOR DETECTING A MOISTURE CONTENT OF A FLOWING FLUID MEDIUM

(71) Applicant: Robert Bosch GmbH, Stuttgart (DE)

(72) Inventors: Bernd Kuenzl, Schwieberdingen (DE); Andreas Kaufmann, Sontheim an der Brenz (DE); Uwe Konzelmann, Asperg (DE); Frank Steuber, Kornwestheim (DE); Achim Briese, Rutesheim (DE)

(73) Assignee: ROBERT BOSCH GMBH, Stuttgart (DE)

( * ) Notice: Subject to any disclaimer, the term of this patent is extended or adjusted under 35 U.S.C. 154(b) by 235 days.

(21) Appl. No.: 14/765,879

(22) PCT Filed: Jan. 9, 2014

(86) PCT No.: PCT/EP2014/050319
§ 371 (c)(1),
(2) Date: Aug. 5, 2015

(87) PCT Pub. No.: WO2014/146799
PCT Pub. Date: Sep. 25, 2014

(65) Prior Publication Data
US 2015/0369785 A1 Dec. 24, 2015

(30) Foreign Application Priority Data
Mar. 22, 2013 (DE) .................. 10 2013 205 086

(51) Int. Cl.
G01N 33/00 (2006.01)
G01N 27/22 (2006.01)
F01N 13/00 (2010.01)

(52) U.S. Cl.
CPC ....... *G01N 33/0059* (2013.01); *F01N 13/008* (2013.01); *G01N 27/223* (2013.01); *F01N 2560/028* (2013.01)

(58) Field of Classification Search
CPC ............. G01N 27/223; G01N 27/4077; G01N 33/0059; F01N 13/008; F01N 2560/028; F02D 2200/0418; G01D 11/245
See application file for complete search history.

(56) References Cited

U.S. PATENT DOCUMENTS 7,810,375 B2 * 10/2010 Weyl .................. G01N 27/4077
                                                        73/23.31
9,581,470 B2 *  2/2017 Rentschler ......... G01N 27/4077
(Continued)

FOREIGN PATENT DOCUMENTS

DE    102006029631    1/2008
DE    102006033251    2/2008
(Continued)

OTHER PUBLICATIONS

International Search Report for PCT/EP2014/050319, dated Feb. 20, 2014.

*Primary Examiner* — Freddie Kirkland, III
(74) *Attorney, Agent, or Firm* — Norton Rose Fulbright US LLP; Gerard Messina (57) ABSTRACT

A sensor device includes a moisture module that includes a sensor element for detecting moisture of a fluid medium flowing in a flow direction and a protective membrane screening the sensor element. The sensor device includes a housing, in a measuring chamber of which the moisture module is at least partially situated, and that includes a protective tube extending into the flowing fluid medium in an axial direction perpendicular to the flow direction, the protective tube is designed for flow of the fluid medium into at least one inlet opening, through an inflow path, into the (Continued)

measuring chamber counter to the axial direction, and out of the measuring chamber via an outflow path in the axial direction and an outlet opening, where, with respect to a direction of gravity, the openings are at a bottom of the protective tube.

11 Claims, 3 Drawing Sheets

(56) References Cited

U.S. PATENT DOCUMENTS

| | | | | |
|---|---|---|---|---|
| 2007/0261473 | A1* | 11/2007 | Weyl | G01N 27/4077 73/23.31 |
| 2010/0005881 | A1* | 1/2010 | Broedel | G01N 33/0059 73/335.02 |
| 2012/0237402 | A1* | 9/2012 | Cantarelli | F02D 41/1448 422/111 |

FOREIGN PATENT DOCUMENTS

| | | |
|---|---|---|
| DE | 102010043062 | 5/2012 |
| DE | 102010043083 | 5/2012 |
| JP | 2000292404 | 10/2000 |
| JP | 2003193830 | 7/2003 |
| JP | 2008506133 A | 2/2008 |
| JP | 2011112557 A | 6/2011 |
| JP | 2012083119 A | 4/2012 |
| WO | WO2008009330 | 1/2008 |
| WO | WO2011070535 | 6/2011 |

\* cited by examiner

SENSOR DEVICE FOR DETECTING A MOISTURE CONTENT OF A FLOWING FLUID MEDIUM

BACKGROUND

Numerous methods and devices for determining the flow properties of fluid media, that is, liquids or gases, are known from the related art. The flow properties may basically be any physically and/or chemically measurable properties which qualify or quantify a flow of the fluid medium. In particular, this may be about the relative or absolute moisture content of a gas or a gas mixture. As is known, moisture sensors find use in the intake tract or the exhaust tract of internal combustion engines. In this case, it is important for regulating the combustion efficiency, for example, particularly for a combustion that is without residue and clean, to ascertain, among other things, the moisture content of the fresh air supplied, in order to enable setting the appropriately desired mixture ratio of fresh air and recirculated exhaust gas and subsequently to determine a quantity of fuel for a predetermined mixing in the cylinder of the internal combustion engine. The information on the moisture content of the environmental air supplied, as well as of the exhaust gas is used, however, by the engine control unit for a plurality of regulated processes.

Such sensor devices for use in the intake tract or the exhaust tract of internal combustion engines are known, for instance, from German documents DE 10 2010 043 062 A1 or DE 10 2010 043 083 A1. The sensor devices provided according to those documents provide a combination of a plurality of sensors, in order to register a plurality of flow properties of fluid media. In particular, one is able to gather from DE 10 2010 043 083 A1, with respect to the ascertainment of the moisture content of the fluid medium, that, in the sensor device provided there, a moisture sensor or a moisture module is taken up which, together with the sensor device, is inserted into a flow channel of a fluid medium. Within the flow channel, the entire fluid medium flows past the semipermeable membrane of the moisture sensor. In this instance, drops of condensed water occurring at the edge of the inlet opening, situated around the membrane, may get stuck there and subsequently wet the semipermeable membrane. The permeability of the membrane may be impaired, in this instance, in such a way that a reliable ascertainment of the moisture content of the medium is no longer ensured. Similarly, because of the direct action on the membrane by the fluid medium, which is usually an unfiltered and/or mechanically compressed process gas, the membrane may be damaged by coarse contamination, such as dust or other dirt particles in the environmental air, sucked in via the intake tract, for example. This may result in a direct contamination of the sensor element and may destroy it.

Furthermore, a protective device for a moisture sensor is known from DE 10 2006 033 251 A1, which is supposed to protect the sensor from aggressive substances in a fluid that is to be analyzed. The protective device proposed in this document provides a cap that encloses the sensor, which is provided with openings which, in turn, are provided with a membrane that is permeable to water vapor.

In the case of many such sensor devices, especially up-to-date moisture sensors, at least one sensor element is used as a rule. This at least one sensor element, as was also described in the abovementioned related art, is as a rule at least partially protected, by only one protective membrane, from a direct contact with the flow of the fluid medium.

SUMMARY

A contamination of the above-mentioned protective membrane, by water droplets or oil droplets, for example, results in at least temporary failure of the moisture measurement capability.

Accordingly, example embodiments of the present invention provide a sensor device for detecting a moisture in a flowing fluid medium, especially for detecting the moisture of the process gas in the intake tract or the exhaust tract of internal combustion engines. The moisture content to be detected can be, for example, of the type discussed above.

The sensor device includes at least one moisture module that includes at least one sensor element for detecting the moisture and at least one protective membrane screening the sensor element. The sensor element is an element configured to register at least one parameter and generate at least one signal corresponding to the registered parameter. The sensor element can, for instance, include at least one sensor chip, which is suitable for ascertaining the moisture of a gas or a gas mixture, for example included in a moisture sensor of the type described above. However, other embodiments of the sensor element are also possible.

The sensor device includes at least one housing, in which there is a measuring chamber, with the moisture module being situated at least partially in the measuring chamber. The housing is an element that encloses at least one inner space (e.g., the measuring chamber) and which exerts a protective function for one or more sensor device components accommodated in the at least one inner space. The housing can particularly be arranged to provide a mechanical protective function. Alternatively or in addition, protective functions with respect to moisture, mechanical stresses during insertion of the sensor device, thermal protective functions, or other protective functions or combinations of the named and/or other protective functions can also exist, for example. The housing can preferably be arranged to ensure a protective effect at least with respect to mechanical stresses. For instance, the housing can at least partially be made of a stiff material, which does not undergo any deformations, for example, during the fixing of the housing in a flow chamber of a fluid medium at usual forces, for example, at usual screwed connection forces. The housing can be made fully or partially of a metallic material and/or a plastic material.

In an example embodiment of the present invention, the housing includes a protective tube projecting in an axial direction into a flowing fluid medium, the protective tube including at least one inflow path, through which the fluid medium is able to flow into the measuring chamber counter to the axial direction, and at least one outflow path, through which the fluid medium is able to flow out again from the measuring chamber in the axial direction. The axial direction is a direction along an axis of rotation defined by the longitudinal extension of the protective tube, which can be aligned perpendicular to a longitudinal axis of the flow chamber, for example.

In an example embodiment, the housing is preferably configured so that the fluid medium is able to flow, counter to an axial direction, preferably perpendicular to the protective membrane of the sensor device, into the inflow path. For example, this axial direction, too, can be along an axis aligned essentially perpendicular to the main flow direction of the fluid medium. A system with a parallel or approximately parallel alignment of inflow path, outflow path, and protective membrane is also conceivable. Furthermore, it is particularly advantageous if the sensor device is aligned with its axial direction parallel to a gravity force vector, and the protective membrane is located, in the sense of the gravity force effect, above, relative to the inlet opening and to the outlet opening. In an example embodiment, the fluid medium is able to flow into the inflow path in such a way, counter to the axial direction, that it is able to flow on through the measuring chamber, where it reaches the sensor element and, for instance, is able to get in contact with the sensor element and/or at least one measuring surface of the sensor element and/or is able to flow into the sensor element, before the fluid medium is subsequently able to flow in the axial direction all the way through the outflow path and back into the flow path.

Corresponding to the requirements made on the protective tube, this usually requires exact coordination. Thus, for example, to ensure high dynamics of the moisture sensor, as a rule, a sufficient mass flow flowing through the protective tube has to be achieved, which may, in turn, however, result in an increased flow speed within the protective tube and the measuring chamber. On the other hand, the protective tube is preferably proportioned or dimensioned in such a way that a transport of condensed water and dirt particles to the sensor element is minimized, but a sufficient flowing through the protective tube is ensured to detect the moisture of the medium. The protection of the protective membrane is particularly required in order to prevent a planar wetting of the protective membrane with water drops or oil drops, and particularly the formation of a water film, in order thereby to prevent a temporary or final failure of the sensor device, as well as to reduce an abrasive effect of the dirt particles when the protective membrane is flowed over, because of the increased flow speed.

A further advantageous effect of such a protective tube is in keeping off water and/or dirt particles in an intake tract or exhaust tract from the sensor element and the protective membrane, i.e., a protection from hammer blow and/or contamination by sucked up dust particles, oil drops, or combustion residues such as soot particles, a sufficient flow-over by the medium being ensured at the same time. As a result, the detection of the moisture in the flowing medium can be carried out with great accuracy, and the operability of the sensor device and particularly the sensor element can also be ensured in a medium contaminated greatly with particles, water drops, oil drops, or oil vapor, as well as in the case of a gushy increase of a fluid level, for example. This is particularly the case when the sensor device according to the present invention is aligned in its axial direction parallel to a gravity force vector, and extends into the flowing medium. In other words, when the protective membrane is located above, in the sense of the gravity force effect, relative to the inlet opening.

In certain cases, for instance, after driving through a puddle or the like, in a region of the air intake tract behind the air filter of a vehicle, a greater quantity of water is also able to collect, which is no longer able to be conducted away any other way, and may subsequently be ripped along by the high volume flow of the medium. This can lead to a gushy-like action on the sensor device, at which essentially the inflow path and the outflow path come in contact with a comparatively large quantity of water. In the case of a closing of the inflow path and the outflow path with water, because of its geometry, the protective tube achieves a protective effect in the type of a diving bell, according to which the volume of the medium, located at this time on the inside of the protective tube, and in particular on the inside of the measuring chamber, is enclosed, and with increasing compression, by the generation of a counter-pressure, prevents the entry of the water all the way into the measuring chamber.

Moreover, in an example embodiment, the protective tube is advantageously set up to provide a sufficient overflowing of the protective membrane, and thereby short diffusion times of the fluid medium to the sensor element, as well as a short reaction time of the sensor element with respect to the detection of the moisture of the fluid medium.

It can thereby be ensured that a sufficient exchange of the medium located in the protective tube take place, in order to enable an accurate measurement of the moisture. The exchange of the medium located in the protective tube preferably takes place at a high speed, in order advantageously to minimize a delay in time between a change in the moisture of the flowing medium and the detection of this change by the sensor element.

According to a further example embodiment of the present invention, the inflow path and the outflow path are arranged within the protective tube rotationally symmetrically to a rotational axis running in the axial direction. First of all, there is thereby created an advantageous embodiment of the protective tube as a rotational body, which can be produced in a simple manner at low expenditure. Avoiding any corners and edges on the preferably rotationally symmetrical outer surface of the protective tube furthermore has the advantage that the protective tube has a lower flow resistance in the fluid medium, and in addition, a turbulence of the fluid is avoided to the greatest extent possible.

According to the last described specific embodiment of the sensor device, in an example embodiment the sensor element of the moisture module is situated aligned with the rotational axis, and is consequently directly acted upon by the flow to be analyzed of the fluid flowing through the protective tube. Because of this, also in an advantageous manner, a uniform impingement of the sensor element exists also at a pulsating flow, as well as at a flow reversal. For an increase of the mass flow over the protective membrane, and thus also over the sensor element, an asymmetrical alignment of the sensor element relative to the axis of rotation of the protective tube is also conceivable.

Furthermore, it is particularly advantageous if the axial direction of the protective tube is essentially aligned perpendicular to the direction of flow of the fluid medium and, in addition, parallel to a gravity force vector. In most tubularly designed flow chambers or flow channels as they are normally used also in the intake tract or the exhaust tract of internal combustion engines, the protective tube can thus be fastened particularly simply in the wall region of the flow channel. An alignment of the protective tube perpendicular to the main flow direction of the fluid medium within the flow chamber further creates the advantage that, independently of the rotatory alignment of the protective tube, an unvarying face area is formed. In addition, in the region of the protective tube, a rerouting takes place of a partial flow of the flowing medium by approximately 90°, in the direction of the inflow path. By this great change in the flow direction, penetration of water drops, for example, into the protective tube is also prevented, since the water drops, for reasons of its mass inertia, are not able to follow this abrupt change in direction.

According to a further example embodiment of the present invention, the inflow path encloses the outflow path at least partially concentrically in an annular manner, which effects a more homogeneous flowing towards the protective membrane in the measuring chamber, which connects the inflow path and the outflow path.

In an example embodiment, the inflow path includes at least one inlet opening in the protective tube, and the outflow path includes at least one outlet opening in the protective tube, and the protective tube preferably extends into the flow of the fluid medium in such a way that the outlet opening is situated farther on the inside of the flow than the inlet opening.

The protective tube, preferably extending perpendicularly into the flow chamber of the fluid medium, because of the surface of action formed with the outer surface of the protective tube, thus supplies the fluid medium with a flow resistance, particularly because of the outer surface of the outflow connecting piece being elongated compared to the housing in the area of the outflow path and of the connecting piece consequently extending further into the inside of the flow chamber. An effect of the outer surface of the protective tube that is flowed against is that the fluid medium flowing against it on its upstream side is blocked, which, in turn, results in a pressure increase in this area, i.e., in the area of the at least one inlet opening. In addition, because of demarcation edges directly at the at least one inlet opening, it can be ensured that, directly at the inlet opening, an area of relatively lower speeds, and, according to the Bernoulli Effect, relatively high static pressure, is created. Because of the displacement effect of the entire protective tube, and particularly because of applying a relatively large radius at the outlet opening at the underpressure connecting piece, a relatively high flow speed of the medium is effected in the area of the outlet opening. In this way, it can particularly be ensured that, at the outlet opening, as a result of the Bernoulli Effect, there is a lower static pressure than in the area of the inlet opening, which leads to a chimney effect and thus a flowing through the protective tube, in the direction intended according to the present invention from the at least one inlet opening to the outlet opening. For the exact setting of the flow-through of the protective tube, the inlet openings can have a wider adapted opening cross section, which can have a circular, an oval, or another geometrically suitable form. This is particularly able to affect the reaction time, and the measuring accuracy going along with that, of the sensor device.

According to the previously described specific embodiment, in an example embodiment, a plurality of concentric inlet openings are situated at a radial distance about the outlet opening. The protective tube, for example, includes at least one inflow connecting piece, and preferably a plurality of inflow connecting pieces. This particularly takes into account the idea of the rotationally symmetrical embodiment of the protective tube which, in an especially advantageous manner, minimizes the dependence of the effectiveness of the sensor device on the rotary alignment during the mounting of the protective tube in the flow chamber. The plurality of inlet openings, in this case, are preferably equidistant from the rotational axis of the protective tube and are furthermore situated at a specified and unvariable angular distance from one another. This means that each of the inlet openings, following an imaginary circular line about the rotational axis, is always at the same distance from the respectively adjacent inlet openings. This conditional, discrete angle situation of the inlet openings, in the individual use for each imaginable rotational angular setting of the protective tube, provides a slight fluctuation of the flow-through of the protective tube, and thus also in the measuring technology properties of the sensor device, but this slight fluctuation of the flow-through, for example, can be partially or completely compensated for by a corresponding adaptation of the opening cross section of the inlet openings.

According to a further example embodiment of the present invention, the outflow path is situated at least partially in the outflow connecting piece within the protective tube. In each case, one inlet opening each can be situated in an inflow connecting piece. An element that is, at least in sections, tube-shaped, for instance, as a hollow cylinder can be used as the outflow or inflow connecting piece. Based on the prevailing pressure conditions at the outlet opening of the outflow connecting piece, the latter can also be designated as the underpressure connecting piece. With regard to a subsequently described embodiment of the outflow connecting piece, expressly no restriction is made to tube-shaped elements with a constant inside or outside diameter, and the diameter can vary. A wall thickness of the outflow connecting piece can be ca. 0.2 mm to 10 mm, and an insertion depth of the outflow connecting piece can preferably be 5 mm to 50 mm. In an example embodiment, an inner diameter of the outflow connecting piece is preferably in the range of ca. 0.5 mm to 10 mm and an outer diameter is preferably in the range of ca. 1 mm to 20 mm. Furthermore, the cross sectional area of the outflow path is preferably approximately the same as the sum of the cross sections of the relevant inlet openings. In an example, the relevant inlet openings include, for example, inlet openings which, after the mounting of the protective tube, are particularly aligned counter to the main flow direction of the medium as well as also those which are aligned downstream, that is, in the direction of the main flow direction of the medium, and which contribute, in the manner intended, according to the present invention, based on the relatively high static pressures, to the through-flow of the protective tube, and thus the measuring chamber.

Consequently, if the cross section of the outflow path, at its end facing the sensor device, is tapered, the advantageous effect of a reinforcement of the Bernoulli Effect can be effected, because thereby the flowing-over speed in the range of the protective membrane can be increased, and thereby the response time of the sensor element can be reduced. As cross sectional tapering, it is generally understood that the cross section of the protective tube is smaller in a certain section than in a section bordering on it. Especially a diffusor type of the embodiment of the inner side, or the inner surface of the outflow connecting piece, which is developed by a continuous cross section tapering counter to the flow direction in the outflow path, or a cross sectional widening in the flow direction as seen in the outflow path, creates a particularly advantageous reinforcement of the Bernoulli Effect, i.e., a speed increase in the area of the membrane. An outflow path developed as a diffusor type has the effect of lower shearing stresses in the outflow connecting piece. In other words, that is, it has a lower pressure loss and a low exit speed of the medium flowing through the protective tube, because of the large cross section of the outlet opening. Thereby, a locally effective utilization is achieved of this underpressure level. In an example, a diffusor type of embodiment only in sections, such as at the end of the outflow path, in the area of the outlet opening, is provided.

Moreover, in an example embodiment, between the opening out of the inflow path into the measuring chamber and the opening out of the outflow path into the measuring chamber, at least one contour section is situated that runs parallel to the protective membrane, in order advantageously to effect as parallel as possible flowing past of the fluid medium at the protective membrane of the sensor element. It can also be provided, in this case, that a radius of the protective tube, in the range of the inflow path and of the outflow path, is in the range of 0.1 mm to 10 mm, and preferably in the range of 0.5 mm to 10 mm.

For an increase of the mass flow over the protective membrane, and thus also over the sensor element, an asymmetrical alignment of the sensor element relative to the axis of rotation of the protective tube is provided. In the case of such an asymmetrical variant, there is an offset of the sensor element with respect to the rotational axis of the protective tube counter to the main flow direction, especially an alignment of the sensor element parallel to the rotational axis in the direction and up to the height of the upstream contour section. With that, in an advantageous manner, an increase in the dynamics of the detected moisture signal is effected. Supplementarily to the embodiment of the sensor device described before, this yields the advantage that the parallel flowing past of the medium setting-in in the area of the contour section takes place in the area of the sensor element preferably situated centrically behind the protective membrane.

In an example embodiment, an annular gap is provided at the protective tube, between the outer circumferential area of the outflow connecting piece and the inlet openings, in order particularly advantageously to prevent the so-called "splash effect," that is, the occasional splashing of water drops hitting the outer surface of the protective tube, in the direction of the inlet openings. In this case, it is also of advantage if the dimensions of the distance and of the diameter of the inlet openings are selected so that the suction effect occurring because of the underpressure in the area of the inlet openings does not suction in any drops being sprayed around.

In the area of the one or more inlet openings, in addition at least one demarcation edge can be formed, whereby a drop of condensed water, possibly carried along by the fluid medium or a water film flowing from the tube wall in the direction of the inlet opening, at first remains hanging on the demarcation edge and is then again ripped along in the form of a drop by medium that is flowing past, without entering the inlet opening. A drop of condensed water running along on the outer surface of the protective tube can thus also be prevented from entering into the inflow path, in order advantageously to prevent a contact of the water with the protective membrane of the sensor module. Furthermore, a demarcation edge in the outer region of the housing can be formed, particularly by an edge of the housing in the area of the seal, which, after mounting of the sensor device, projects from the plane of the wall section of the flow chamber.

According to another example embodiment of the present invention, because of a rib provided radially outside of the one or more inlet openings, which forms a circumferential removing channel, a drop, caught by the rib and conducted into the removing channel, is guided around the inlet openings to the downstream-side outer surface of the protective tube, advantageously by the utilization of a capillary action that takes place. A film of condensed water forming, based on temperature differences in the wall area of the flow chamber, is likewise caught by the rib. In this way, a possible entry of a water drop into the inflow path and the acting upon the protective membrane by the water drop are prevented.

In a further advantageous example embodiment, the housing includes at least one fastening element for fastening the housing on the wall of a flow chamber or flow channel through which the medium flows, the fastening element being designed so that, in the fastened state, the protective tube extends at least partially, and preferably at an insertion depth of up to 50 mm, into the flow chamber. In this instance, a cross section of the flow chamber is preferably essentially round or oval. However, a rectangular cross section, or rather, a cross section with at least one flat section can also be provided. The housing is preferably able to be connected to the flow chamber, particularly to the outer wall of the flow chamber, in such a way that, in the fastened state, the protective tube of the housing extends at least partially into the flow chamber, through an opening provided in a wall section of the flow chamber. For this purpose, the housing can include, for instance, at least one fixing element set up to perform a mechanical fixing and/or stabilization of the housing relative to the flow chamber. For this purpose, the housing can be made of a metallic material, for example. Alternatively or in addition, however, other material can be used, for instance, ceramic materials and/or plastic materials.

To fasten the sensor device in the wall section of the flow chamber, it is also advantageous if the fastening element includes at least one sealing element, especially at least one O-ring enclosing the protective tube, in order to ensure a gas-tight closing of the flow chamber in the area of the sensor device. Thereby, an exchange can be prevented of the medium to be analyzed with the environmental atmosphere that exists outside the flow chamber.

At the same time, in an advantageous example embodiment, the housing is designed at least partially as a plug sensor. Alternatively, in an example embodiment, the housing is in the form of an intermediate plate or a sensor accommodation plate, which, if necessary, can be retrofitted, using slight mechanical changes and using just a few manipulations.

According to one additional example embodiment of the present invention, at least one electronics chamber is formed in the housing. Furthermore, at least one control circuit is provided, which is provided for the control of the moisture sensor as well as for passing on a produced measuring signal. In an example embodiment, the control circuit includes an evaluation circuit and is preferably situated in the electronics chamber. A further advantage will thereby exist if the moisture module is situated at least partially in the electronics chamber, the electronics chamber being preferably situated at least partially outside the fluid medium. The electronics chamber is a chamber for accommodating an electronic circuit or electronic components, preferably designed as a cavity with the shape of a right parallelepiped. It can also be a half cylinder with a preferably rectangular base area, however.

Example embodiments of the present invention are depicted in the figures and will be explained by examples in greater detail in the following text.

DETAILED DESCRIPTION

Figures 1, 1A, 1B:
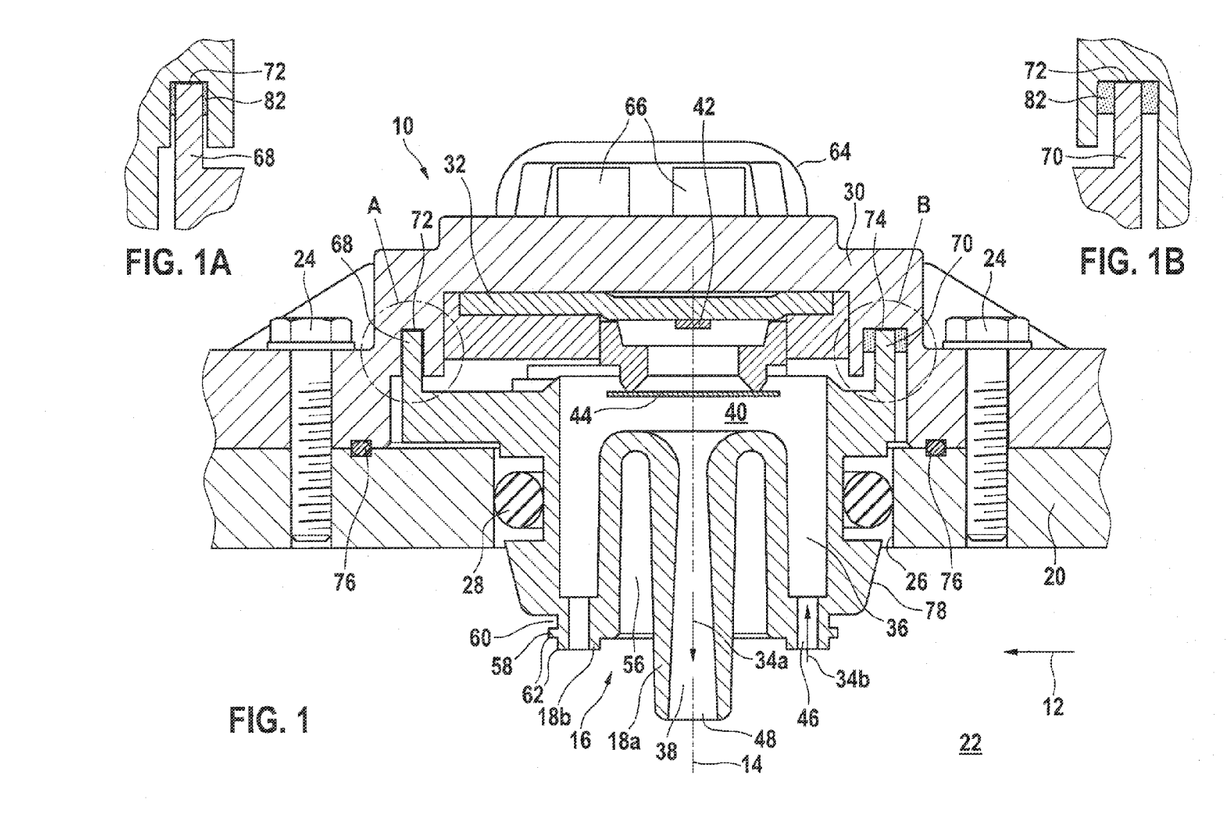
FIG. 1 shows a cross sectional representation of a sensor device according to a preferred example embodiment of the present invention.
FIG. 1A an enlarged illustration of detail A in FIG. 1.
FIG. 1B an enlarged illustration of detail B in FIG. 1.
Figure 2:
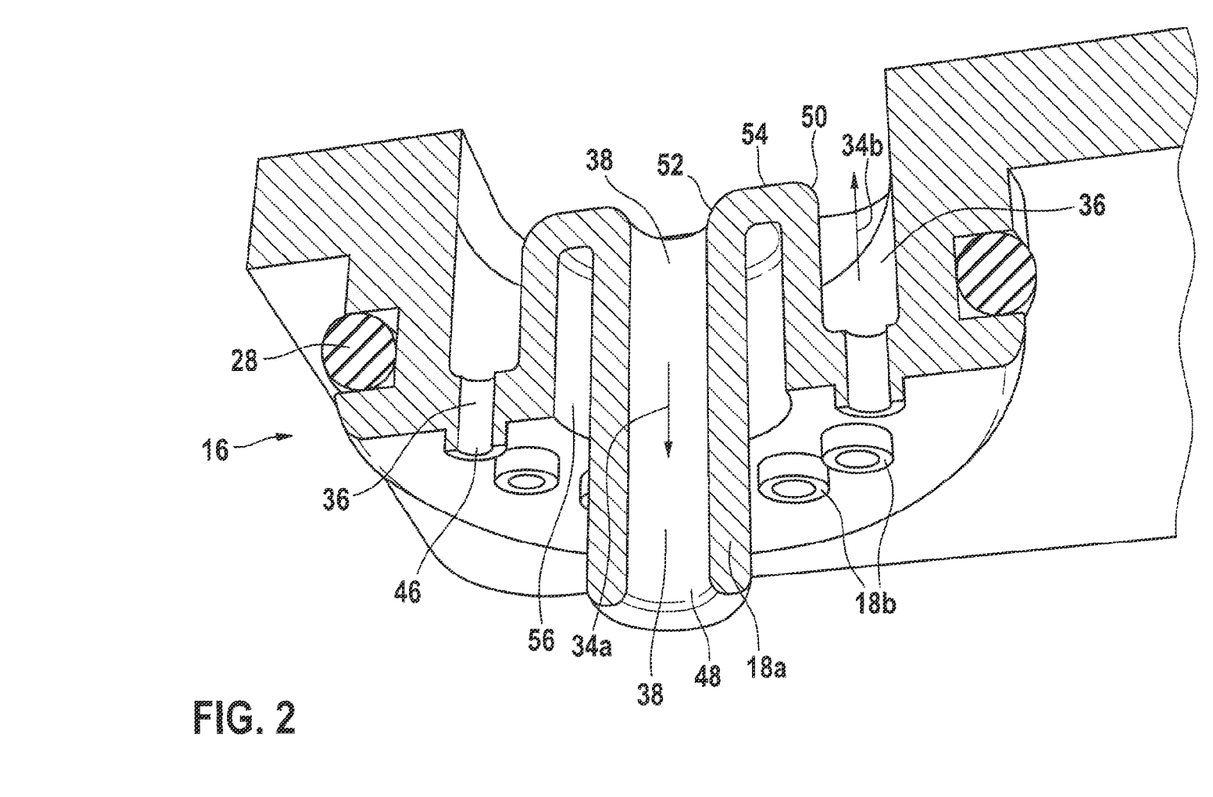
FIG. 2 a perspective sectional representation of a sensor device according to a preferred example embodiment of the present invention.

In FIGS. 1 and 2, a sensor device 10 is shown at different viewing angles according to two only slightly different example embodiments of the present invention. The representation of FIG. 1 shows sensor device 10 with a moisture module 32 situated on protective tube 16. FIG. 2 shows an alternative example embodiment of protective tube 16, in which moisture module 32 is not shown, for better simplification and explanation. The two representations are described jointly in the following text.

The sectional representation of sensor device 10 shown in FIG. 1 runs in a plane parallel to a main flow direction 12 of the fluid medium and along a rotational axis 14 of protective tube 16. Protective tube 16 includes an outflow connecting piece 18a and at least one inflow connecting piece 18b. Protective tube 16 preferably includes a plurality of inflow connecting pieces 18b, which are situated concentrically relative to outflow connecting piece 18a, as shown in FIG. 1. For example, outflow connecting piece 18a is coaxial with rotational axis 14, and inflow connecting pieces 18b are uniformly distributed in a circumferential direction about rotational axis 14, outside outflow connecting piece 18a. Outflow connecting piece 18a acts as an underpressure connecting piece and inflow connecting pieces 18b act as overpressure connecting pieces, as will be described in greater detail below. An arrow characterizing main flow direction 12 would lie in the image plane of FIG. 1. Based on the preferably rotationally symmetrical design of protective tube 16, for the easier description, one may assume a main flow direction 12 of the fluid medium, running from right to left in the illustration.

Furthermore, one may see in detail from the specific embodiment shown in FIG. 1 that sensor device 10, is situated in a wall section 20 of a flow chamber 22, and is held on wall section 20 by fastening elements 24. In this connection, one may especially see in the illustration that protective tube 16, of the specific embodiment shown, of sensor device 10 in the mounted state extends through an opening 26 in wall section 20 into flow chamber 22. Protective tube 16, in this case, includes a groove for accommodating a sealing element 28, for example, an O-ring. Sealing element 28 is used, on the one hand, for the support of protective tube 16 in opening 26, and on the other hand for the sealing opening 26, in a manner impervious to gas, from the outer environment.

Moreover, one may see from the illustration in FIG. 1 that sensor device 10 includes a housing 30, in which a moisture module 32 is situated at least partially. Furthermore, housing 30 of the preferred specific embodiment of sensor device 10 shown includes a protective tube 16 extending into the flowing fluid medium in an axial direction 34a. In protective tube 16, in turn, at least one inflow path 36 and one outflow path 38 are formed. Outflow path 38 in protective tube 16 is situated, in this case, preferably rotationally symmetrically about rotational axis 14. Inflow path 36 is further formed rotationally symmetrically about rotational axis 14 and outflow path 38. To put it more accurately, outflow path 38 is formed in outflow connecting piece 18a, and a respective inflow path 36 is developed in each one of inflow connecting pieces 18b.

In FIG. 1, inflow path 36 and outflow path 38 are connected with respect to flow via a measuring chamber 40. At the opposite side of measuring chamber 40 as seen from outflow path 38, sensor element 42 of moisture module 32 is situated coaxially aligned with outflow path 38. In FIG. 1, sensor element 42 of moisture module 32 is separated spatially from measuring chamber 40 by a protective membrane 44.

Fluid medium can flow essentially perpendicular to rotational axis 14 in flow chamber 22 and is blocked at, with respect to flow direction 12, the upstream-sided outer surface of outflow connecting piece 18a, and the flow speed in this region is lowered. Accordingly, the fluid medium, in the area of inflow connecting piece 18b, particularly in the area of inlet opening 46, flows at a lower speed than the medium in the area of outlet opening 48 at the lower end of outflow connecting piece 18a. Corresponding to the flow speed, that is thus higher at outlet opening 48, there also prevails in this area a higher dynamic pressure than in the area of inlet opening 46. Observed from a physical point of view, the flow speed behaves proportionally to the dynamic pressure of the fluid medium, and antiproportionally to the static pressure. As a result, in this case, because of the flow resistance, which outflow connecting piece 18a represents, a region of inlet opening 46 is created in which a higher static pressure prevails than in the region of outlet opening 48. Since the fluid medium naturally compensates for these pressure differences, a part of the fluid medium flows through inlet opening 46 along inflow path 36 and to measuring chamber 40. Starting at measuring chamber 40, the fluid medium flows on in axial direction 34a along outflow path 38 and via outlet opening 48 back into flow chamber 22.

For the further sealing of measuring chamber 40 from the outer environment, according to the embodiment shown, a further sealing element 76, for example, an O-ring seal, is provided in an area running around opening 26, between wall section 20 and housing 30. Protective tube 16, as shown, preferably further includes a bearing journal 68 as well as at least one further bearing journal 70, using which protective tube 16 supports itself on housing 30. For this purpose, housing 30 preferably includes an alignment bore 72, which is preferably used for accommodating bearing journal 68, as well as a bore of the bearing 74 for accommodating further bearing journal 70. An inner diameter of alignment bore 72, in this case, preferably essentially corresponds to the outer diameter of bearing journal 68. In other words, a development is preferred for protective tube 16 and housing 30, in which alignment bore 72 and bearing journal 68 are produced using tight tolerances. As a result, the play between bearing journal 68 and alignment bore 72 is designed, as far as is possible technically and from a standpoint of production engineering, to be low. Thereby, in addition to the end-face-side contact surface of bearing journal 68 in alignment bore 72, a contact surface is created over the whole circumference, that is, which besides the end face of bearing journal 68 also includes at least a part of its circumferential surface, whereby a lateral guidance of bearing journal 68, and thus also of protective tube 16 is achieved. Protective tube 16 is thereby able to be additionally aligned with respect to sensor element 42 in a direction perpendicular, preferably laterally in the main flow direction, to rotational axis 14. Further bearing journal 70 is situated freely movable with respect to a corresponding lateral alignment, and is supported only using an end-face side contact surface with respect to housing 30.

FIG. 1A shows an enlarged view of detail A of FIG. 1 and FIG. 1B shows an enlarged view of detail B of FIG. 1. To fix protective tube 16 to housing 30, an adhesive 82, for example, can be introduced into alignment bore 72 and/or the bore of the bearing 74, which then adheres to the outer circumferential surface of bearing journal 68 and/or of additional bearing journal 70, as is shown in FIGS. 1A and 1B. Adhesive 82 is, for instance, inserted into alignment bore 72 and/or the bore of the bearing 74 in such a way that it touches the end-face end of bearing journal 68 and/or additional bearing journal 70 as well as at least one part of the outer circumferential surface of bearing journal 68 and/or additional bearing journal 70 and the surrounding wall sections of alignment bore 72 and/or bore of bearing 74.

In a preferred example embodiment, as shown in FIG. 1, protective tube 16 lies against a surface on the outside of wall section 20. Thus, protective tube 16 is held between housing 30 and wall section 20 by the clamping in of protective tube 16. To achieve a lateral offset of sensor element 42, for example, with respect to rotational axis 14 of protective tube 16, alignment bore 72, for instance, is able to be positioned correspondingly in housing 30 so that the desired offset is achieved. For this purpose, it can also be required to provide the bores for fastening elements 24 in housing 30 with a corresponding offset.

Furthermore, in FIG. 1, over the length of the two bearing journals 68, 70, there is the possibility of aligning housing 30 in and counter to the direction along rotational axis 14 relative to protective tube 16. In particular, one is able thereby to adjust the height of measuring chamber 40. This, as a result, further influences the flowing through measuring chamber 40 and consequently also the reaction times and the sensitivity of sensor device 10, whereby advantageously a faster and more accurate detection of the moisture in the medium is made possible.

According to the representation shown in FIG. 2, in an example embodiment of the present invention, in the area of opening out 50 of inflow path 36 into measuring chamber 40 as well as of opening out 52 of outflow path 38 into measuring chamber 40, a contour section 54 is provided, which connects inflow path 36 and outflow path 38. Contour section 54, in an example embodiment, includes one radius or two radii, so that, between the opening out 50 of inflow path 36 and opening out 52 of outflow path 38, a flat contour section 54 is formed running parallel to protective membrane 44. This contour section 54, preferably running in measuring chamber 40 in sections parallel to protective membrane 44 produces a flow of the fluid medium that is also in sections directed parallel to protective membrane 44, which acts advantageously on the measuring process.

In order to prevent, according to the present invention, a penetration of water drops, carried along in the flow of the fluid medium, which are usually able to move in the range of size of inlet opening 46, as shown in the illustration in FIG. 1, preferably an annular gap 56 is positioned between inflow path 36 and outflow path 38. Thereby, a suctioning in or penetration of smaller water droplets, which are created by an impact of a larger water drop on the outer surface of outflow connecting piece 18a by corresponding lateral spraying away, is prevented advantageously, since these spray into annular gap 56 that is provided for this purpose, or, as may be seen in FIG. 3, are not able to reach inlet opening 46, because of a shielding.

It is also possible that, based on the temperature difference on the inside of flow chamber 22 with respect to the outer environment of flow chamber 22, condensed water forms on the inner wall of flow chamber 22.

Likewise because of the flow of the fluid medium in flow direction 12, this condensed water, which preferably forms as a film on the inner wall surface of flow chamber 22, is carried along in the flow direction 12. In an example embodiment, as shown in FIG. 1, in order to prevent this film of condensed water from penetrating into measuring chamber 40 via inlet openings 46, a rib 58 is provided in the area of inlet opening 46 to catch a film of condensed water that is guided down the outer surface of protective tube 16, and guide it around the area of inlet opening 46 via diversion channel 60 that is formed by rib 58. On the downstream side, rib 58 functions as a demarcation edge 62, at which a drop that is forming is able to be ripped along by the flowing fluid medium. The inlet openings 46 are furthermore preferably formed as connecting pieces, so as to form an additional demarcation edge 62 at their lower end. In FIG. 1, housing 30 includes at least one electronics chamber 64, which preferably accommodates a control circuit 66 of sensor device 10. As a result, moisture module 32 is at least partially situated in electronics chamber 64 and also in measuring chamber 40 with sensor element 42 and protective membrane 44, above protective tube 16.

Figure 3:
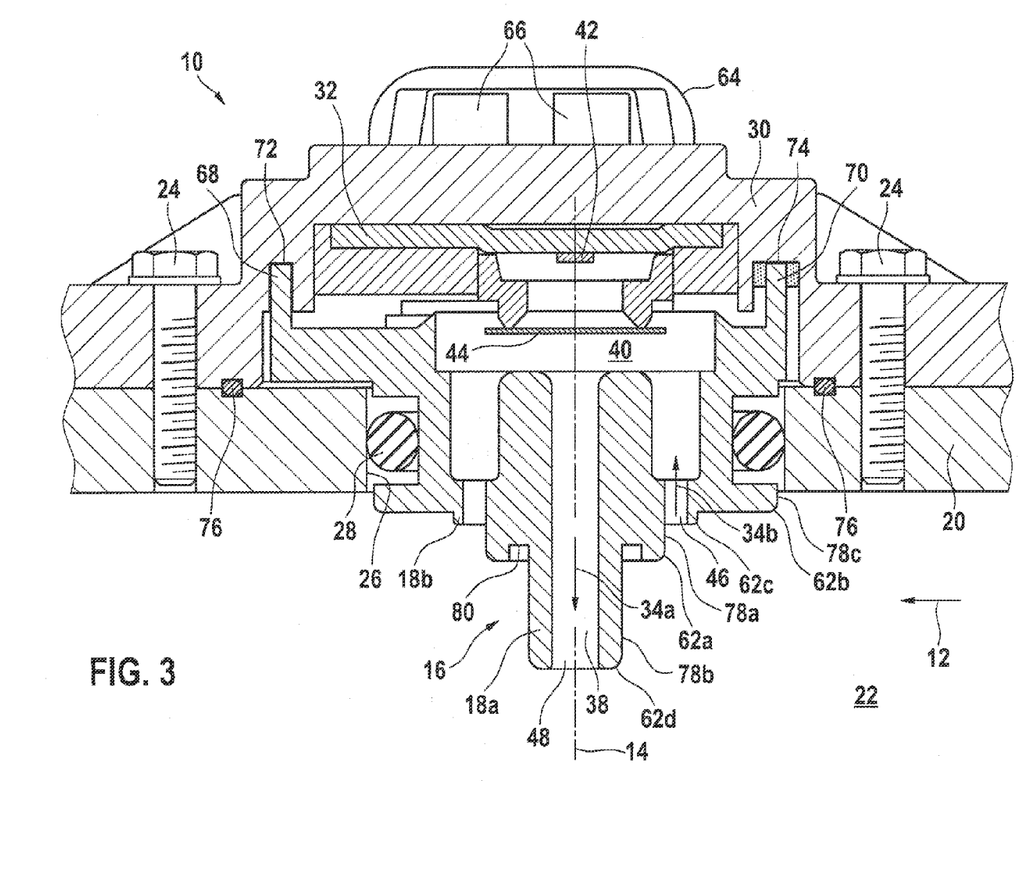
FIG. 3 a cross sectional representation of a sensor device according to a further example embodiment of the present invention.

FIG. 3 shows a cross sectional representation of the sensor device 10 according to another example embodiment of the present invention. Many of the features shown in FIG. 3 are like those described above with respect to FIG. 1, and the following is a description of differences of the embodiment shown in FIG. 3 from the embodiment shown in FIG. 1.

The surface contour on the inside of flow chamber 22 in FIG. 3 is different than that shown in FIG. 1. In particular, a plurality of demarcation edges 62a, 62b, 62c are developed on protective tube 16, as will be explained in greater detail below. In particular, protective tube 16 includes at least one demarcation edge 62c in the vicinity of inlet opening 46 and at least one rounding 62d with a relatively large radius near outlet opening 48. An edge radius of demarcation edge 62c near inlet opening 46 is substantially smaller, or even sharp-edged as a 90° angle compared to the radius of rounding 62d in the vicinity of outlet opening 48. Further, for example, the area of protective tube 16 between inlet opening 46 and the outer surface of outflow connecting piece 18a, that is, a rebounding surface 78b, includes a curve which borders directly on inlet openings 46 towards rotational axis 14 and forms an encircling rebounding surface 78a. For the formation of a demarcation edge 62a at the lower end, in the illustration, of previously described rebounding surface 78a, a gap 80 is provided between demarcation edge 62a and the outer surface of outflow connecting piece 18a. The design of the rebounding surface 78a, bordering directly on inlet opening 46, increases, in the area of inlet opening 46, the overpressure level and thus creates an advantageous flowing through protective tube 16. Furthermore, outflow connecting piece 18a, extending in the direction of outlet opening 48 as seen in main flow direction 12, includes additional rebounding surface 78b on its outer surface. At the lower end of rebounding surface 78b, rounding 62d is developed, which forms the transition between rebounding surface 78b and the wall of outflow connecting piece 18a that borders on outlet opening 48. The radius of rounding 62d should be made as large as possible, based on the necessity of producing as large as possible an underpressure at outlet opening 48. Demarcation edge 62a can also have a large edge radius. For example, the radius of rounding 62d is in the range of 2 to 15 mm, for instance 8 mm. Demarcation edge 62a may have an edge radius of 1 mm to 10 mm, for instance 5 mm.

Moreover, protective tube 16, in its outer transition area towards wall section 20, also forms a rebounding surface 78c, which transitions into an even, radially inward curve. In this area of transition into the even curve, an additional demarcation edge 62b is formed, at which a water film is able to collect, for example, flowing along the inner surface of wall section 20, and, by a drop formation at demarcation edge 62*b*, is able to drip off and be ripped along by the flow of the medium. The radius of demarcation edge 62*b* can be in the range of 0.1 mm to 5 mm, for example.

Inlet openings 46 preferably come out of the even shape of protective tube 16 described before. The additional demarcation edge 62*c* thus formed at the radially outer section of inlet opening 46 can preferably have an edge radius in a range of 0.1 mm to 1.0 mm, for instance 0.8 mm, and thus an edge radius which is clearly smaller than the edge radius of demarcation edges 62*a* and 62*b*. Demarcation edge 62*b* can have an edge radius in the range of ca. 0.1 mm to 5 mm, for instance 2 mm.

What is claimed is:

1. A sensor device, comprising:
   a moisture module that includes a sensor element configured to detect moisture of a flowing fluid medium, and a protective membrane arranged to screen the sensor element; and
   a housing, the moisture module being situated at least partially in a measuring chamber of the housing, wherein the housing includes a protective tube that:
   extends in an axial direction into the flowing fluid medium;
   includes at least one inflow path of an inflow connecting piece configured for a flow of the fluid medium therethrough counter to the axial direction and into the measuring chamber; and
   includes at least one outflow path of an outflow connecting piece configured for flow of the fluid medium therethrough from the measuring chamber and in the axial direction;
   wherein the inflow path and the outflow path are aligned in a same axial direction,
   wherein the measuring chamber is in the sensor device, and
   wherein the flowing fluid medium flows across the inflow connecting piece and across the outflow connecting piece.

2. The sensor device of claim 1, wherein the protective tube is configured to provide a sufficient flow over of the protective membrane for detection by the sensor element of the moisture within a short reaction time of the sensor element.

3. The sensor device of claim 1, wherein the inflow path and the outflow path are arranged rotationally symmetrical to a rotational axis running in the axial direction.

4. The sensor device of claim 1, wherein the axial direction of the protective tube is aligned essentially perpendicular to a main flow direction of the fluid medium in a flow chamber from which the fluid medium enters the at least one inflow path.

5. The sensor device of claim 1, wherein the at least one inflow path encloses the outflow path at least partially concentrically in an annular manner.

6. The sensor device of claim 1, wherein the at least one inflow path includes at least one inlet opening, and the outflow path includes an outlet opening that is situated farther into the flow of the fluid medium than does the at least one inlet opening.

7. The sensor device of claim 6, wherein the protective tube includes at least one demarcation edge in a vicinity of the inlet opening and at least one rounding in a vicinity of the outlet opening, and an edge radius of the demarcation edge is substantially smaller than an edge radius of the rounding.

8. The sensor device of claim 1, wherein the at least one inflow path includes a plurality of inflow paths, each provided with a respective inlet opening, the outflow path is provided with an outlet opening, and the inlet openings are positioned concentrically about the outlet opening at a radial distance.

9. The sensor device of claim 1, wherein the protective tube forms an annular gap between an outer circumferential area of the outflow connecting piece and inlet openings into the at least one inflow path.

10. The sensor device of claim 1, wherein, between a position at which the at least one inflow path opens out into the measuring chamber and a position at which the at least one outflow path opens into the measuring chamber, the protective tube includes at least one contour section that runs parallel to a direction in which the protective membrane extends.

11. The sensor device of claim 1, wherein the housing includes at least one fastening element for fastening the housing to a wall section of a flow chamber through which the fluid medium flows, such that the protective tube extends at least partially into the flow chamber.

* * * * *